| United States Patent [19] | [11] Patent Number: 4,945,173 |
| Wood | [45] Date of Patent: * Jul. 31, 1990 |

[54] PROCESS FOR THE PRODUCTION OF GAMMA-BUTYROLACTONE

[75] Inventor: Michael A. Wood, Middlesbrough, England

[73] Assignee: Davy McKee (London) Limited, London, England

[ * ] Notice: The portion of the term of this patent subsequent to Aug. 30, 2005 has been disclaimed.

[21] Appl. No.: 223,079

[22] Filed: Jul. 22, 1988

[30] Foreign Application Priority Data

Jul. 29, 1987 [GB] United Kingdom ................. 8717992

[51] Int. Cl.$^5$ ........................................... C07D 307/33
[52] U.S. Cl. .................................... 549/295; 549/325; 549/326; 568/864
[58] Field of Search ...................... 549/295, 325, 326; 568/864

[56] References Cited

U.S. PATENT DOCUMENTS

| 4,032,458 | 6/1977 | Cooley et al. | 568/864 |
| 4,032,583 | 6/1977 | Arganbright et al. | 260/637 R |
| 4,767,869 | 8/1988 | Harrison et al. | 549/295 |

*Primary Examiner*—Glennon H. Hollrah
*Assistant Examiner*—Ba K. Trinh
*Attorney, Agent, or Firm*—Bernard, Rothwell & Brown

[57] ABSTRACT

A process is described for the production of substantially pure gamma-butyrolactone from a feed mixture containing a major amount of gamma-butyrolactone and a minor amount of diethyl succinate which comprises fractionally distilling the mixture in a fractionation zone in the presence of diethyl ethoxysuccinate and recovering from the fractionation zone an overhead vaporous product comprising gamma-butyrolactone which is substantially free from diethyl succinate and is liquid bottom product comprising diethyl ethoxysuccinate and diethyl succinate in admixture one with another. This procedure can be used to separate a gamma-butyrolactone rich fraction obtained by distillation in one or more stages of a crude reaction product obtained by hydrogenation of a $C_4$ dicarboxylic acid ester feedstock that contains a major molar amount of diethyl maleate and a minor molar amount of diethyl succinate, using a diethyl maleate feedstock from an esterification plant to provide diethyl maleate for use as feedstock for the hydrogenation process which is admixed with recycled diethyl succinate recovered from the fractionation zone.

16 Claims, 3 Drawing Sheets

PROCESS FOR THE PRODUCTION OF GAMMA-BUTYROLACTONE

This invention relates to a process for the production of gamma-butyrolactone. It also relates to a process for the recovery of gamma-butyrolactone from a mixture containing gamma-butyrolactone and diethyl succinate and possibly also one or more other components.

The production of gamma-butyrolactone and/or butane-1,4-diol by catalytic hydrogenation of dialkyl esters of $C_4$ dicarboxylic acids, such as maleic acid, fumaric acid, succinic acid, and acetylenedicarboxylic acid, has been described on various occasions. In some cases the hydrogenation reaction results in production of tetrahydrofuran as a co-product. Thus Example 12 of U.S. Pat No. 2,079,414 describes hydrogenation of diethyl succinate at a hydrogen:ester molar ratio of about 10:1 in the vapour phase over a mixed Cd-Cu-Zn chromite catalyst at 367° C. and 2500 p.s.i. (about 173 bar) to yield a mixture of tetramethylene glycol (butane-1,4-diol) and tetrahydrofuran. A similar process is described in Example 1 of U.S. Pat. No. 2,040,944. Moreover WO-A-No. 82/03854 proposes, inter alia, a process for the production of butane-1,4-diol and/or tetrahydrofuran by vapour phase hydrogenation of an dialkyl ester of maleic acid, fumaric acid, acetylenedicarboxylic acid or succinic acid at 75° C. to 300° C. and at a pressure of 0.1 kg/cm² absolute to 100 kg/cm² absolute (about 0.1 bar to about 100 bar) over a catalyst comprising a reduced mixture of copper oxide and zinc oxide.

In EP-A-No. 0143634 and in WO-A-No. 86/03189 there is described a process in which diethyl maleate, diethyl fumarate, diethyl succinate or a mixture of two or more thereof is subjected to catalytic hydrogenation in the vapour phase to yield a reaction product mixture which contains butane-1,4-diol, as well as ethanol and variable amounts of co-products including gamma-butyrolactone, trahydrofuran and water, besides minor amounts of diethyl succinate and n-butanol. Although butane-1,4-diol is often the product of primary interest, both gamma-butyrolactone and tetrahydrofuran are sold as commodity chemicals of relatively high value. Hence it is normally desired to recover the co-product gamma-butyrolactone and tetrahydrofuran from the crude reaction mixture as well as the butane-1,4-diol present therein. A related process for the production of gamma-butyrolactone is described in WO-A-No. 86/07358.

When diethyl maleate is used as starting material for the hydrogenation reaction described in EP-A-0143634, in WO-A-No. 86/03189 or in WO-A-No. 86/07358, the resulting crude reaction mixture may contain, in addition to butane-1,4-diol and gamma-butyrolactone, possibly also a negligible amount of unconverted diethyl maleate, as well as minor amounts of other components including tetrahydrofuran, diethyl succinate, water and n-butanol. The recovery of the desired products, in particular butane-1,4-diol and gamma-butyrolactone, from such mixtures can be difficult since conventional distillation methods may result in production of azeotropic mixtures of other components of the crude reaction mixture with the desired products. Thus although it is a relatively simple matter to separate by distillation at atmospheric pressure tetrahydrofuran and the other relatively low boiling materials, such as water, ethanol and n-butanol, from a crude reaction product mixture obtained by hydrogenation of diethyl maleate and to separate the higher boiling materials into a gamma-butyrolactone rich fraction and into a butane-1,4-diol rich fraction by distillation in one or more stages under reduced pressure, the recovery of substantially pure gamma-butyrolactone from the gamma-butyrolactone rich fraction is problematic because diethyl succinate forms an azeotrope with gamma-butyrolactone and co-distils therewith.

In U.S. Pat. No. 4,032,583 there is described a process for recovering butane-1,4-diol in high purity from a crude reaction mixture which contains, inter alia, gamma-butyrolactone. This process involves adding water and then subjecting the resulting aqueous mixture to solvent extraction with a hydrocarbon solvent followed by distillation of the resulting raffinate. In this way most of the co-products and only a trace of the butane-1,4-diol are extracted into the hydrocarbon solvent, while the aqueous layer contains essentially pure butane-1,4-diol. Before extraction sufficient water is added to produce an aqueous layer preferably containing from about 20 wt % to about 50 wt % water. The water is recovered as an overhead product in the subsequent distillation step and butane-1,4-diol is recovered as a bottom product. As the process involves use of two additional components, namely water and a hydrocarbon solvent, it is somewhat complex to carry out. Moreover as water has a high latent heat of vaporization and has to be removed in considerable quantity during the distillation step, the process requires considerable energy input for its performance. In addition, although distillation of the hydrocarbon extract phase for solvent recovery is proposed in U.S. Pat. No. 4,032,583, as well as recycle of unconverted ester, no procedure is described for recovery of other potentially useful products from this hydrocarbon extract.

It would be desirable to provide a method of purifying crude gamma-butyrolactone and similar complex mixtures of gamma-butyrolactone and other components including esters, which is simple to operate and has a low energy input requirement. It would also be desirable to provide a method of purifying such materials which enables recovery of all the potentially useful products therefrom. It would further be desirable to provide a process for production of gamma-butyrolactone by hydrogenation of diethyl maleate which overcomes the problems in recovery thereof from the crude reaction product caused by formation of azeotropes with by-product diethyl succinate.

The present invention accordingly seeks to provide a process for the recovery of gamma-butyrolactone from a mixture containing gamma-butyrolactone and diethyl succinate, which is simple in operation and which has a relatively low energy input requirement. It further seeks to provide a process for recovery of gamma-butyrolactone from complex mixtures containing also diethyl succinate, which enables efficient recovery of other useful components of the mixture. It also seeks to provide an improved method for production of gamma-butyrolactone by hydrogenation which obviates the recovery problems associated with formation of azeotropes with by-product diethyl succinate.

According to one aspect of the present invention there is provided a process for the production of substantially pure gamma-butyrolactone from a feed mixture containing a major molar amount of gamma-butyrolactone and a minor molar amount of diethyl succinate which comprises distilling the mixture in a fractionation zone in the presence of diethyl ethoxysuccinate, and recovering from the fractionation zone an overhead vaporous product comprising gamma-butyrolactone which is substantially free from diethyl succinate and a liquid bottom product comprising diethyl ethoxysuccinate and diethyl succinate in admixture one with another.

The invention further provides a process for the production of gamma-butyrolactone which comprises:

(i) hydrogenating a C$_4$ dicarboxylic acid ester feedstock in a hydrogenation zone in the presence of a heterogeneous ester hydrogenation catalyst, said ester feedstock containing a major molar amount of diethyl maleate and a minor molar amount of diethyl succinate;

(ii) recovering from the hydrogenation zone a crude reaction product that is substantially free from diethyl maleate and contains ethanol, butane-1,4-diol, gamma-butyrolactone, and a minor molar amount of diethyl succinate;

(iii) distilling the crude reaction product in one or more stages to yield a gamma-butyrolactone-rich fraction containing, in addition to gamma-butyrolactone, a minor amount of diethyl succinate;

(iv) providing a stream comprising diethyl ethoxysuccinate;

(v) supplying diethyl ethoxysuccinate of step (iv) and gamma-butyrolactone rich fraction of step (iii) to a fractionation zone;

(vi) fractionally distilling the gamma-butyrolactone rich fraction of step (iii) in the fractionation zone in the presence of said diethyl ethoxysuccinate;

(vii) recovering as an overhead fraction from the fractionation zone a product stream that is substantially free from diethyl succinate and consists essentially of pure gamma-butyrolactone;

(viii) recovering from the fractionation zone a liquid bottom product comprising said diethyl ethoxysuccinate and diethyl succinate in admixture one with another; and (ix) recycling diethyl succinate present in the liquid bottom product of step (viii) to form at least a part of the C$_4$ dicarboxylic ester feedstock of step (i).

A particularly preferred process further includes:

(x) separating diethyl succinate from the liquid bottom product of step (viii);

(xi) recovering from step (x) a stream comprising diethyl ethoxysuccinate;

(xii) recycling diethyl succinate from step (x) to form part of the feedstock of step (i); and (xiii) recycling said diethyl ethoxysuccinate containing stream of step (xi) to step (iv).

The ester hydrogenation catalyst used in the hydrogenation zone of step (i) can be any solid catalyst that is capable of catalysing the hydrogenation of dialkyl esters of C$_4$ dicarboxylic acids. The ester hydrogenation zone may be operated under liquid phase conditions but is preferably operated under vapour phase conditions. Examples of suitable catalysts include reduced mixtures of copper oxide and zinc oxide of the type disclosed in WO-A-No. 82/03854 and copper chromite catalysts, for example those of the type disclosed in U.S. Pat. No. 2,079,414. In a particularly preferred process the hydrogenation zone is operated under vapour phase conditions using a copper chromite catalyst which contains, before reduction, from about 25 to about 45% by weight of copper and from about 20 to about 35% by weight of chromium. Such vapour phase conditions typically include use of a temperature of from about 150° C. to about 240° C. and a pressure of from about 25 bar to about 75 bar, for example a pressure in the range of from about 35 bar to about 45 bar. The ester hydrogenation zone may comprise two successive hydrogenolysis zones operated according to the teachings of EP-A-No. 0143634, of WO-A-No. 86/03189 or of WO-A-No. 86/07358.

The crude reaction product from the hydrogenation zone contains as products butane-1,4-diol, gamma-butyrolactone, and tetrahydrofuran. It also contains materials that can be recycled to the hydrogenation zone, such as diethyl succinate, for formation of further product, as well as ethanol that can be recycled for formation of further diethyl maleate. It also contains as by-products water, n-butanol and a minor amount of diethyl ethoxysuccinate and other "heavies".

Such crude hydrogenation products typically contain at least about 10 mol %, up to about 70 mol % or more, of ethanol, at least about 5 mol % each, up to about 20 mol % each or more, of butane-1,4-diol and gamma-butyrolactone, not more than about 15 mol % of water, and not more than about 2 mol % of n-butanol. They usually further include a minor amount of diethyl succinate and minor amounts of other by-products, such as diethyl ethoxysuccinate. Typically such minor amounts do not exceed about 5 mol % each.

It is not possible to achieve satisfactory separation of such a mixture by fractional distillation because it includes materials which form binary azeotropes with one or more other components of the mixture. In particular gamma-butyrolactone forms a binary azeotrope with diethyl succinate. It has, however, surprisingly been found that distillation of the gamma-butyrolactone rich fraction of step (iii) in the presence of diethyl ethoxysuccinate enables a satisfactory fractional distillation procedure to be adopted. As diethyl ethoxysuccinate is a by-product of the vapour phase diethyl maleate hydrogenation processes of EP-A-No. 0143634, of WO-A-No. 86/03189 and of WO-A-No. 86/07358, it is possible to use such by-product diethyl ethoxysuccinate in the process of the invention, thereby reducing the need to supply chemicals from an external source to the gamma-butyrolactone plant. Moreover, as diethyl ethoxysuccinate can readily be prepared from diethyl maleate by reaction with ethanol (both of which are available at the plant site) in the presence of sodium ethoxide, production of supplies of this chemical for use at start up of the plant and for any make-up quantities needed in operation of the plant does not present a problem to the plant operator.

The fractionation zone may comprise a single fractionation column, in which case a stream of the gamma-butyrolactone rich fraction of step (iii) or other mixture of gamma-butyrolactone and diethyl succinate may be fed to an intermediate part of the fractionation column while diethyl ethoxysuccinate is fed to a part of the distillation column above said intermediate part.

The invention also contemplates a form of plant in which the fractionation zone comprises first and second fractionation columns connected in series, in which a stream of the gamma-butyrolactone rich fraction of step (iii) or other mixture of gamma-butyrolactone and diethyl succinate is fed to an intermediate part of the first fractionation column, in which a stream comprising diethyl ethoxysuccinate is fed to a part of the first fractionation column above said intermediate part, in which a first top fraction is recovered from the top of the first distillation column, said first top fraction being substantially free from diethyl succinate and comprising a mixture of diethyl ethoxysuccinate and gamma-butyrolactone, in which said first top fraction is supplied to the second fractionation column, in which said overhead fractionation comprises the top fraction from the second fractionation column, and in which said liquid bottom product comprises the bottom product from the first fractionation column. Preferably a bottom fraction comprising diethyl ethoxysuccinate is recycled from the bottom of the second fractionation column to said first fractionation column.

The fractionation zone is conveniently operated at a pressure in the range of from about 0.01 bar to about 0.75 bar. Throughout this specification and its claims all pressures are expressed in bar absolute, unless otherwise indicated.

Typically the feed mixture to the fractionation zone, e.g. the gamma-butyrolactone rich fraction of step (iii), contains from about 99 mole % to about 75 mole % gamma-butyrolactone and from about 1 mole % to about 25 mole % diethyl succinate.

It will usually be preferred to add said dialkyl ester to the distillation zone in a molar ratio with respect to the diethyl succinate in the feed mixture of from about 4:1 to about 200:1.

In order that the invention may be clearly understood and readily carried into effect three preferred processes for the production of gamma-butyrolactone and three respective plants designed for operation thereof, will now be described, by way of example only, with reference to the accompanying drawings, FIGS. 1 to 3, which are each a schematic flow diagram of the plant.

It will be understood by those skilled in the art that, as the drawings are diagrammatic, further items of equipment such as condensers, heat exchangers, reflux drums, column reboilers, pumps, vacuum pumps, temperature sensors, pressure sensors, pressure relief valves, control valves, flow controllers, level controllers, holding tanks, storage tanks, and the like, would additionally be required in a commercial plant. The provision of such additional items of equipment forms no part of the present invention and is in accordance with conventional chemical engineering practice.

Figure 1:
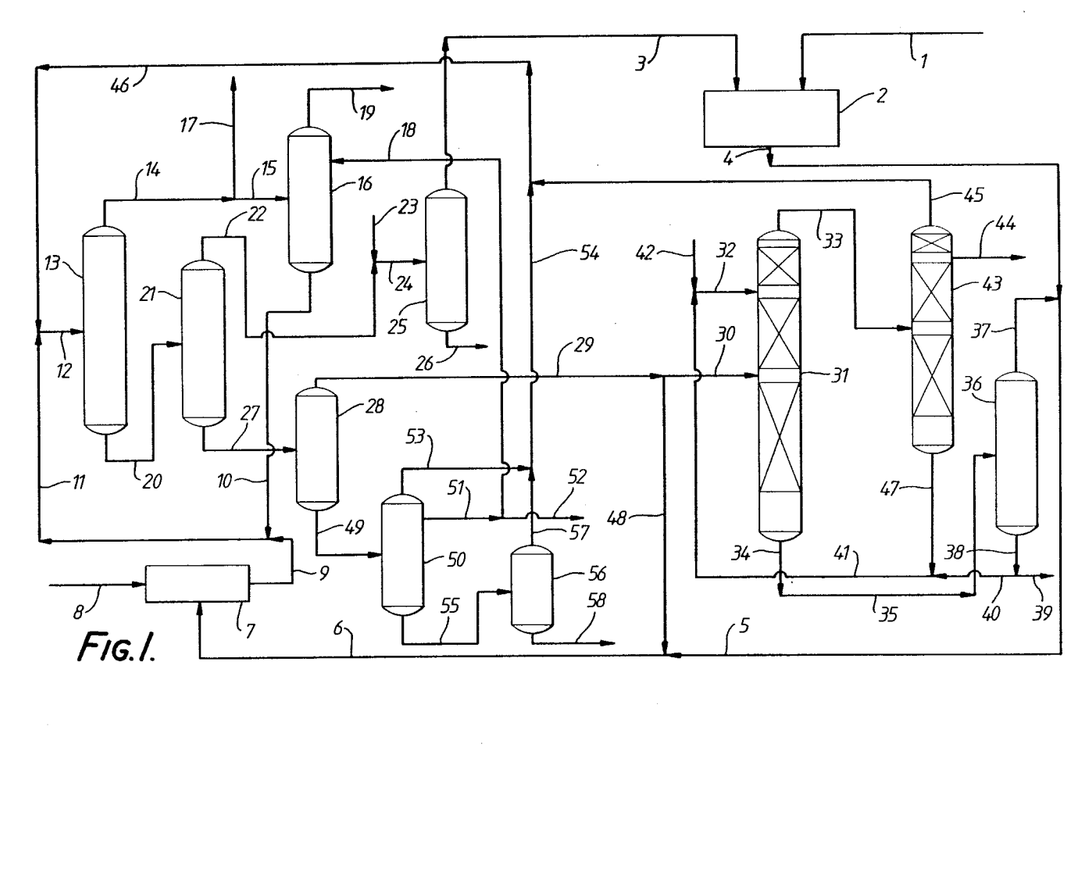

Referring to FIG. 1 of the drawings, maleic anhydride is supplied in line 1 to an esterification plant 2 which is also supplied in line 3 with ethanol. Esterification plant 2 produces a stream of acid-free diethyl maleate in line 4, part of which is fed by way of lines 5 and 6 to a vapour phase catalytic hydrogenation plant 7 which is also fed with hydrogen in line 8. In plant 7 the diethyl maleate is hydrogenated in the presence of excess gaseous hydrogen by passage, in the vapour phase, over a copper chromite catalyst to produce a crude product stream in line 9 that is substantially free from diethyl maleate and contains, as products, a mixture of butane-1,4-diol, gamma-butyrolactone, and tetrahydrofuran, and, as recyclable materials, diethyl succinate, and ethanol, as well as minor amounts of by-products, including water, n-butanol, diethyl ethoxysuccinate and other "heavies".

Esterification plant 2 may include a non-catalytic monoesterification stage, in which maleic anhydride is reacted with excess ethanol to yield monoethyl maleate according to the following equation:

(1)

and one or more catalytic esterification stages, in which the resulting monoethyl maleate is further reacted with ethanol to yield diethyl maleate, according to the following equation:

(2)

Although homogeneous liquid phase esterification catalysts, such as sulphuric acid, can be used, it is preferred to use in the catalytic esterification stage or stages a heterogeneous solid catalyst, such as an ion exchange resin containing sulphonic acid groups, for example Amberlyst 16. (The word "Amberlyst" is a trade mark). This obviates the need to neutralise the catalyst as is necessary when using a homogeneous catalyst, such as sulphuric acid. Hence the production of significant quantities of waste liquors and loss of potential product, in the form of monoethyl maleate, therein is avoided by use of a heterogeneous catalyst. Since equation (2) is reversible, as much water of esterification as possible must be removed if the yield of diethyl maleate is to be maximised.

In one scheme monoethyl maleate is passed in cocurrent with excess ethanol through a primary esterification reactor containing a charge of a suitable ion exchange resin (e.g. Amberlyst 16), the resulting intermediate reaction mixture is distilled to remove excess ethanol and water therefrom, and then the bottom product containing a mixture of mono- and diethyl maleates is fed in countercurrent to dry ethanol through one or more further esterification stages, each also containing a charge of a resin catalyst (e.g. Amberlyst 16). Further details of such a plant can be found in EP-A-No. 0255399.

Final traces of monoethyl maleate and any other acid material present can be removed from the system by a two stage distillation procedure according to the teachings of EP-A-No. 0255401, possibly followed by the washing procedures taught in GB-A-No. 2193207. In this two stage distillation procedure monoethyl maleate is allowed to decompose thermally in the first distillation stage to yield ethanol, which is removed overhead, and maleic anhydride, which codistils with product diethyl maleate and is separated therefrom in a second distillation state. Further distillation stages can be used to remove the final traces of acid materials therefrom. The alternative washing procedure involves washing the ester with an alkaline solution of disodium maleate containing an alkali metal hydroxide, carbonate, bicarbonate or a mixture thereof, following by distillation, to remove traces of water and sodium ions.

In an alternative esterification process described in WO-A-No. 88/00937, a primary esterification reactor is used that contains a charge of Amberlyst 16 resin, or similar solid catalyst. The resulting mixture of diethyl maleate, monoethyl maleate, ethanol and water is distilled to remove substantially all the ethanol and water therefrom, and the ester mixture (typically containing an approximately 65:35 molar mixture of diethyl and monoethyl maleates) is reacted with further ethanol in a continuously stirred tank reactor containing also a charge of Amberlyst 16 resin or other solid catalyst from which a stream containing an approximately 85:15 molar mixture of diethyl and monoethyl maleates, water and ethanol is recovered. This is then distilled to remove substantially all water and ethanol therefrom and the residue is subjected to the procedure of EP-A-No. 0255401 and possibly also to the procedure of GB-A-No. 2193207.

Hydrogenation plant 7 may include a single catalytic zone or may include two hydrogenolysis zones operated according to the teachings of EP-A-No. 0143634, of WO-A-No. 86/03189 or of WO-A-No. 86/07358.

The crude hydrogenation product is admixed with recycled material in line 10 and fed by way of lines 11 and 12 to a first distillation column 13 which is operated at a pressure of 1.1 bar and at a head temperature of 66.1° C. A mixture of tetrahydrofuran, ethanol and water is recovered overhead in line 14, together with any hydrogen dissolved in the crude product in line 9. This mixture is condensed in a condenser (not shown) before being passed in line 15 to a second distillation column 16. A vent gas stream consisting mainly of hydrogen is taken in line 17 for use as a fuel or for venting to a flare stack. Column 16 is operated at 1.1 bar and with a head temperature of 68.3° C. A stream of butane-1,4-diol is fed to an upper part of second distillation column 16 in line 18 at a mass flow rate which is approximately 6 to 7 times that of the mass flow rate in line 15 so as to give a butane-1,4-diol:tetrahydrofuran molar ratio of approximately 4.5:1 in second distillation column 16. Essentially pure tetrahydrofuran is recovered as an overhead product rrom second distillation column 16 in line 19.

The bottom product in line 10 from second distillation column 16 is a wet mixture of tetrahydrofuran, ethanol, and a minor amount of n-butanol, dissolved in butane-1,4-diol. This is recycled to the first distillation column 13, after admixture with crude product in line 9, by means of lines 11 and 12.

The bottom fraction from first distillation column 13 contains, in addition to the high boiling materials present, such as butane-1,4-diol, gamma-butyrolactone, diethyl succinate, and a minor amount of diethyl ethoxysuccinate and other "heavies", also ethanol, water, and n-butanol, but only a trace amount of tetrahydrofuran. The bottom fraction is passed in line 20 to a third distillation column 21 which is operated at a pressure of 0.26 bar. Low boiling materials, i.e. remaining traces of tetrahydrofuran, water, ethanol and n-butanol are recovered overhead in line 22 at a head temperature of 47.8° C. and are mixed with make-up ethanol supplied in line 23. The resulting mixed stream is supplied in line 24 to a fourth distillation column 25. Column 25 is operated at 2 bar and at a head temperature of 96.7° C. A wet ethanol stream is recovered overhead in line 3 for use in the esterification plant 2. Esterification plant 2 includes a water recovery section (not shown) whereby the water mass balance of the plant can be maintained.

The bottom product from third distillation column 25, which is recovered in line 26, is substantially pure n-butanol.

The "heavy ends" fraction in line 27 from third distillation column 21 is a mixture containing, in addition to butane-1,4-diol and gamma-butyrolactone, a minor amount of diethyl succinate, as well as a minor amount of diethyl ethoxysuccinate and other "heavies". This is fed to a fifth distillation column 28 which is operated under vacuum at a pressure of 0.13 bar with a head temperature of 136° C. The overhead product from column 28 is a mixture of diethyl succinate, gamma-butyrolactone and a minor amount of butane-1,4-diol; this is passed by way of lines 29 and 30 to a sixth distillation column 31 which is operated under vacuum. Column 31 is also supplied by way of line 32, at a point above the point of connection of line 30, with diethyl ethoxysuccinate. Hence the mixture of gamma-butyrolactone, diethyl succinate and butane-1,4-diol in line 30 is distilled in sixth column 31 in the presence of diethyl ethoxysuccinate. The overhead product in line 33 from column 31 is a mixture of diethyl ethoxysuccinate and gamma-butyrolactone. The bottom product from column 31 comprises a mixture of diethyl succinate and diethyl ethoxysuccinate and possibly a trace amount of "heavies"; this is taken by way of lines 34 and 35 to a seventh distillation column 36 which is operated under vacuum. Diethyl succinate is recovered overhead from column 36 in line 37 and is recycled to the hydrogenation plant 7 by way of lines 5 and 6.

The bottom product from column 36 in line 38 is predominantly diethyl ethoxysuccinate, but also contains a minor amount of diethyl succinate, together with a small amount of other "heavies". The level of other "heavies" in this stream is controlled by taking a purge stream in line 39. The major part of the stream in line 38 is recycled to column 31 by way of lines 40, 41 and 32. Make-up diethyl ethoxysuccinate is supplied in line 42.

As already mentioned, the stream in line 33 is substantially free from diethyl succinate and consists predominantly of a mixture of gamma-butyrolactone and diethyl ethoxysuccinate. This is passed to an eighth distillation column 43 which is also operated under vacuum. A side stream is taken from near the top of column 43 in line 44. This stream consists essentially of gamma-butyrolactone. A purge stream can be taken in line 45 for recycle of any "lights" which reach column 43 to first distillation column 13; this purge stream is recycled from line 45 by way of lines 46 and 12 to column 13.

The bottom product from column 43 is mainly diethyl ethoxysuccinate but contains also a minor amount of gamma-butyrolactone. This is recycled to sixth distillation column 31 by way of lines 47, 41 and 32.

If desired some of the material in line 29 can be recycled to the hydrogenation plant 7 by way of lines 48 and 6.

Reverting to fifth column 28, the bottom product therefrom in line 49 is a mixture of butane-1,4-diol and "heavies". This is distilled in ninth distillation column 50 which is operated at a pressure of 0.1 bar and at a head temperature of 162.2° C. A stream of substantially pure butane-1,4-diol is recovered from near the top of column 50 in line 51. Part of this is passed to second distillation column 16 in line 18, whilst the remainder is passed on as product butane-1,4-diol in line 52. A bleed stream may be taken from the reflux stream for column 50 in line 53 and recycled to first distillation column 13 by way of lines 54 and 46 for the purpose of recycling any "lights" which may reach column 50.

The bottom product from distillation column 50 contains butane-1,4-diol, diethyl ethoxysuccinate and other "heavies". This stream in line 55 is passed to a tenth distillation column 56 which is operated at a head temperature of 165° C. and at a pressure of 0.1 bar. The overhead product in line 57 is combined with overhead product in line 53 and passed by way of lines 54, 46 and 12 to first distillation column 13. A bottom product stream consisting mainly of diethyl ethoxysuccinate and other "heavies" in line 58 is passed to a recovery section (not shown) for the recovery of diethyl ethoxysuccinate therefrom to provide at least a part of the make-up material supplied in line 42 or is purged from the plant.

Figure 2:
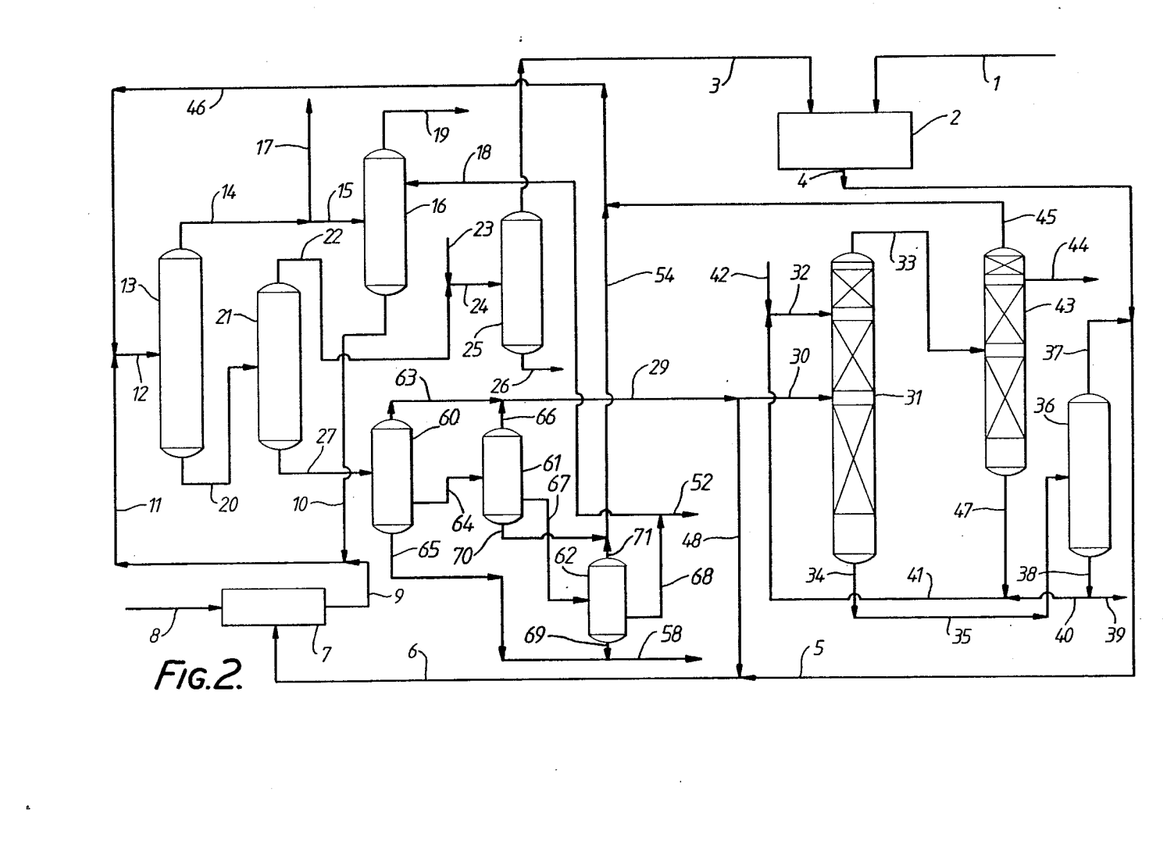

The plant of FIG. 2 is generally similar to that of FIG. 1 and like reference numerals have been used in the two Figures to denote similar items.

In the plant of FIG. 2 two distillation columns 60 and 61 replace fifth distillation column 28 of the plant of FIG. 1, whilst tenth distillation column 56 is omitted. Instead a further distillation column 62 is present.

Column 60 is supplied with the "heavy ends" fraction in line 27 from the third distillation column 21 at a temperature of 120° C. It is operated at a head temperature of 129° C. and a pressure of 0.1 bar. The overhead product in line 63 is a mixture of gamma-butyrolactone and diethyl succinate. A side stream of crude butane-1,4-diol is taken in line 64 and pumped to a middle point of column 61 at a temperature of 185° C. Column 61 is also operated at 0.1 bar and at a head temperature of 132° C. The bottom product from column 60 in line 65 is predominantly "heavies" such as diethyl ethoxysuccinate.

The overhead product in line 66 from column 61 is also a mixture of gamma-butyrolactone and diethyl succinate and is admitted with the stream in line 63 to provide the stream in line 29.

A side stream is taken from column 61 in line 67; this consists predominantly of butane-1,4-diol and is pumped to a mid-point of column 62 which is operated at 0.1 bar and at a head temperature of 165° C. From column 62 there is recovered a vapour side stream consisting of substantially pure butane-1,4-diol in line 68. This is divided to form the product butane-1,4-diol stream in line 52 and the butan-1,4-diol required in line 18 for second distillation column 16. The bottom product from column 62 in line 69 consists mainly of "heavies" and is combined with the material of line 65 to form the stream in line 58.

The bottom product from column 61 is mainly butane-1,4-diol and is recycled by way of line 70, 54 and 46 to first distillation column 13. The overhead product in line 71 from column 62 also contains any "lights" that find their way to column 62 and is recycled to first distillation column 13 by way of lines 54 and 46.

Figure 3:
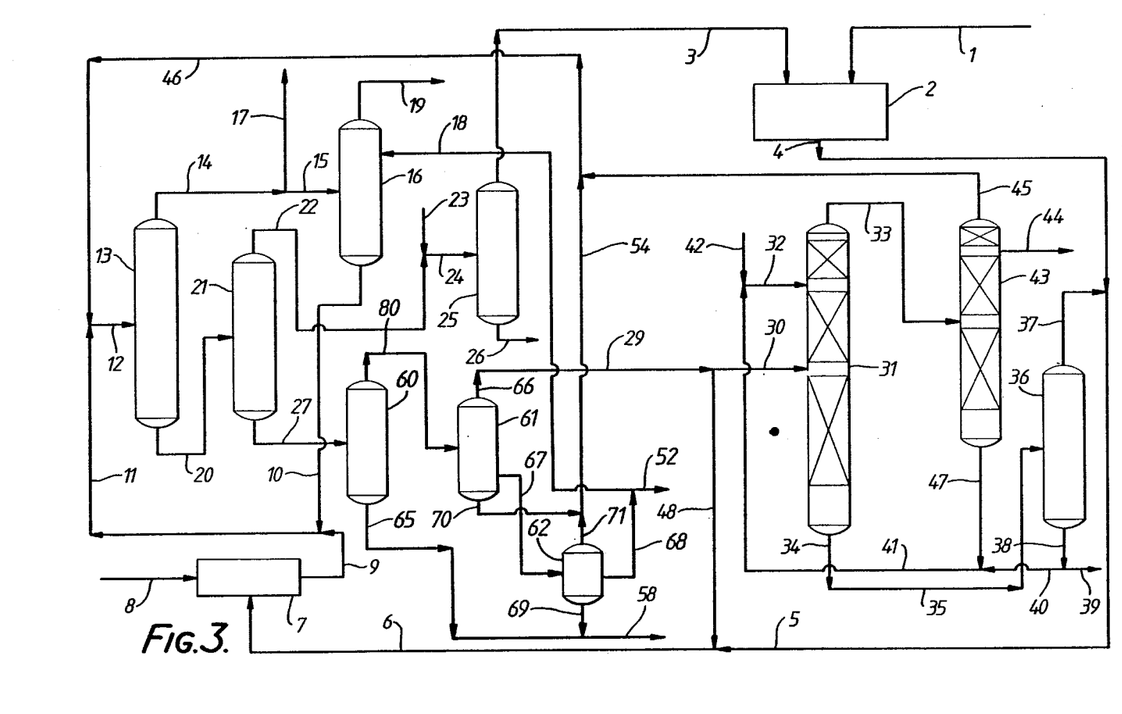

The plant of FIG. 3 is generally similar to that of FIG. 2 except that column 61 is fed with the overhead product from column 60 in line 80 and lines 63 and 64 are omitted.

The invention is further illustrated in the following Example.

EXAMPLE (a) Distillation of a crude product obtained by vapour phase hydrogenation of diethyl maleate according to the teachings of EP-A-No. 0143634 was effected on a pilot plant scale using a 12.2 m (40 feet) distillation column with an internal diameter of 0.1 m (4 inches) made of 316 stainless steel packed with six beds of Sulzer Mellapak 500Y stainless steel packing. (The word "Mellapak" is a trade mark).

The column was provided with an oil heated reboiler. Each section of the column corresponding to a particular bed was lagged and could be electrically heated to enable adiabatic conditions to be maintained in the column. A liquid distributor/re-distributor and a vapour distributor were positioned between each adjacent pair of beds within the column.

The crude product was supplied continuously to the column above the third bed of packing from the bottom at a feed temperature of 70° C. using a column top pressure of 1.03 bar (770 mm Hg). The column head temperature was 65.8° C. and the reflux ratio was 20:1. 762.39 kg of crude product was fed to the distillation column; 50.80 kg of overhead product was recovered from the top of the column as a condensate and 709.48 kg of bottoms product was recovered from the sump of the column, corresponding to a weight balance of 99.7% in the first distillation step. (The small apparent loss can be attributed to experimental error). The mol % composition of the various streams was as set out below in Table I.

TABLE I

| Component | Feed | Overhead | Bottoms |
|---|---|---|---|
| Tetrahydrofuran | 4.82 | 80.64 | 0.04 |
| Ethanol | 59.08 | 5.11 | 63.10 |
| Water | 9.52 | 14.17 | 9.10 |
| n-butanol | 0.17 | 0 | 0.19 |
| gamma-butyrolactone | 10.27 | 0 | 11.00 |
| Butane-1,4-diol | 14.71 | 0 | 15.07 |
| Diethyl succinate | 1.22 | 0 | 1.27 |
| "Unknown(s)" | 0.21 | 0.08 | 0.23 |

(b) The bottoms product from the first distillation step was re-distilled in the same column at a pressure of 0.26 bar (197 mm Hg) and at a head temperature of 44° C. The feed was continuously supplied, above the second bed of packing from the bottom of the column, at a temperature of 82.2° C. under a reflux ratio of 0.35:1. 705.75 kg of feed yielded 379.01 kg of overhead condensate and 324.57 kg of bottoms product, corresponding to a weight balance of 99.7%. (The balance being attributed to experimental error). The compositions in mol % of the streams were as set out in Table II.

TABLE II

| Component | Overhead | Bottoms |
|---|---|---|
| Tetrahydrofuran | 0.02 | 0.09 |
| Ethanol | 87.17 | 0.20 |
| Water | 12.55 | 0.06 |
| n-butanol | 0.23 | Trace |
| gamma-butyrolactone | 0 | 39.68 |
| Butane-1,4-diol | 0 | 54.90 |
| Diethyl succinate | 0 | 4.27 |
| "Unknown(s)" | 0.03 | 0.80 |

(c) A stream of a similar composition to the bottoms product of Table II and containing essentially the same "unknown(s)" was fed to the same distillation column in a further continuous distillation experiment. The stream was fed to the column above the fifth bed of packing from the bottom. The feed temperature was 160° C., the reflux ratio was 0.85, the head temperature was 148° C. and the column was operated at a pressure of 0.1 bar (75 mm Hg). In this experiment 317.50 kg of feed stream yielded 299.80 kg of overhead product and 13.00 kg of bottoms product corresponding to a mass balance of 99.4%. (The missing 0.6% is attributed to experimental error). The compositions in mol % of the various streams were as set out in Table III.

TABLE III

| Component | Feed | Overhead | Bottoms |
|---|---|---|---|
| Tetrahydrofuran | 0.03 | 0.12 | — |
| Ethanol | 0.23 | 0.49 | — |
| Water | 0.55 | 0.52 | — |
| n-butanol | — | — | — |
| gamma-butyrolactone | 43.19 | 43.31 | 0.94 |
| Butane-1,4-diol | 51.18 | 51.16 | 65.42 |
| Diethyl succinate | 4.21 | 4.09 | — |
| "Unknown(s)" | 0.61 | 0.31 | 33.63 |

(d) The same column was used in a later experiment for distillation of the overhead product of Table III. This was fed at a temperature of 144° C. above the fifth bed of packing from the bottom and a vapour draw stream was taken from above the bottom bed of packing. 294.26 kg of feed material yielded 149.70 kg of overhead product, 131.86 kg of bottoms product and 15.00 kg of vapour draw product, corresponding to a mass balance of 100.8%. (The balance was not perfect due to experimental errors). The compositions of the various feed streams in mol % were as set out in Table IV. The column was operated at a pressure of 0.1 bar (76 mm Hg) and at a reflux ratio of 0.96.

TABLE IV

| Component | Feed | Overhead | Bottoms | Vapour Draw |
|---|---|---|---|---|
| Tetrahydrofuran | 0.12 | 0.31 | 0.01 | 0.03 |
| Ethanol | 0.50 | 1.11 | 0.01 | 0.01 |
| Water | 1.27 | 1.30 | 0.17 | 0.30 |
| gamma-butyrolactone | 42.68 | 84.06 | 0.17 | 1.63 |
| Butane-1,4-diol | 51.04 | 4.94 | 99.33 | 97.60 |
| Diethyl succinate | 4.05 | 7.91 | — | — |
| "Unknown(s)" | 0.34 | 0.37 | 0.30 | 0.43 |

(e) A first feed stream having a composition similar to that of the overhead fraction of Table IV was redistilled in the same column, being supplied above the first bed of packing from the bottom at a temperature of 106° C. A second feed stream of diethyl ethoxysuccinate was supplied above the fifth bed of packing from the bottom also at a temperature of 106° C. The column was operated at 0.1 bar (75 mm Hg). In the course of the experiment 247.50 kg of diethyl ethoxysuccinate was fed to the column, as well as 107.50 kg of the first feed stream. There resulted 87.91 kg of overhead product and 269.35 kg of bottoms product, corresponding to a balance mass of 100.64% (the departure from 100% being due to experimental errors). The composition in mol % of the various streams was as set out in Table V.

TABLE V

| Compound | First Feed | Second Feed | Overhead | Bottoms |
|---|---|---|---|---|
| Tetrahydrofuran | 0.21 | — | 0.19 | Trace |
| Ethanol | 1.05 | — | 1.12 | — |
| Water | 3.31 | 0.24 | 1.44 | 0.28 |
| n-butanol | 0.01 | — | 0.02 | — |
| gamma-butyrolactone | 90.11 | 0.02 | 96.44 | 6.12 |
| Butane-1,4-diol | 0.57 | — | 0.01 | 0.61 |
| Diethyl maleate | — | 0.01 | — | — |
| Diethyl fumarate | 0.01 | 0.03 | 0.05 | 0.02 |
| Diethyl succinate | 4.61 | — | 0.26 | 4.32 |
| Diethyl ethoxysuccinate | — | 99.68 | 0.20 | 88.55 |
| "Unknown(s)" | 0.12 | 0.02 | 0.27 | 0.10 |

(f) A feed stream with a similar composition to the overhead stream of Table V was re-distilled in the same column. It was supplied above the second bed of packing from the bottom of the column, whilst a vapour draw stream was taken from above the bottom bed of packing. 55.40 kg of feed stream yielded 12.10 kg of overhead product, 32.8 kg of vapour draw stream and 10.30 kg of bottoms product, corresponding to a mass balance of 99.64% (the departure from 100% being ascribable to experimental errors). The feed temperature was 121.5° C., the reflux ratio was 8.1, and the operating pressure was 0.13 bar (100 mm Hg). The compositions in mol % were as set out in Table VI.

TABLE VI

| Compound | Feed | Overhead | Vapour Draw | Bottoms |
|---|---|---|---|---|
| Tetrahydrofuran | 0.12 | 1.04 | — | 0.01 |
| Ethanol | 1.01 | 4.44 | — | 0.04 |
| Water | 1.23 | 4.92 | — | 0.14 |
| n-butanol | — | — | — | — |
| gamma-butyrolactone | 97.11 | 88.24 | 99.83 | 98.69 |
| Butane-1,4-diol | — | — | — | — |
| Diethyl maleate | — | — | — | — |
| Diethyl fumarate | 0.03 | 0.08 | — | 0.01 |
| Diethyl succinate | 0.05 | 0.12 | 0.08 | 0.07 |
| Diethyl ethoxysuccinate | 0.14 | — | 0.02 | 0.93 |
| "Unknown(s)" | 0.31 | 1.16 | 0.07 | 0.11 |

(g) A feed stream similar to that of the bottoms product of Table V was re-distilled in the same distillation column, being fed above the third bed of packing from the bottom at a temperature of 105° C. The column was operated at a pressure of 0.1 bar (75 mm Hg) and at a reflux ratio of approximately 14.6. 241.61 kg of feed stream yielded 14.6 kg of overhead product and 223.30 kg of bottoms product, corresponding to a mass balance of 98.46%. (The missing percentage can be attributed to experimental errors). The compositions in mol % were as set out in Table VII.

TABLE VII

| Compound | Feed | Overhead | Bottoms |
|---|---|---|---|
| Tetrahydrofuran | — | 0.08 | — |
| Ethanol | — | 0.72 | 0.01 |
| Water | 0.26 | 1.49 | 0.25 |
| gamma-butyrolactone | 6.49 | 59.07 | 0.19 |
| Butane-1,4-diol | 0.68 | 4.83 | 0.09 |
| Diethyl maleate | — | 0.29 | — |
| Diethyl fumarate | — | 0.16 | 0.21 |
| Diethyl succinate | 4.36 | 32.68 | Trace |
| Diethyl ethoxysuccinate | 88.13 | 0.22 | 99.02 |
| "Unknown(s)" | 0.08 | 0.46 | 0.23 |

What is claimed is:
1. A process for the production of substantially pure gamma-butyrolactone from a feed mixture containing a major amount of gamma-butyrolactone and a minor molar amount of diethyl succinate which comprises:
 (a) providing a fractionation zone;
 (b) providing a stream comprising diethyl ethoxysuccinate;
 (c) supplying the feed mixture to the fractionation zone;
 (d) supplying the stream of step (b) to the fractionation zone;
 (e) fractionally distilling the feed mixture in the fractionation zone in the presence of diethyl ethoxysuccinate of the stream of the step (b); and
 (f) recovering from the fractionation zone;
  (A) an overhead vaporous product comprising gamma-butyrolactone which is substantially free from diethyl succinate; and
  (B) a liquid bottom product comprising diethyl ethoxysuccinate and diethyl succinate in admixture one with another.
2. A process according to claim 1, in which the fractionation zone comprises a single fractionation column, in which a stream of the feed mixture is fed to an intermediate part of the fractionation column and in which the stream of step (b) is fed to a part of the distillation column above said intermediate part.
3. A process according to claim 1, in which the fractionation zone comprises first and second fractionation columns connected in series, in which a stream of the feed mixture is fed to an intermediate part of the first fractionation column, in which the stream of step (b) is fed to a part of the first fractionation column above said intermediate part, in which a first top fraction is recovered from the top of the first distillation column, said first top fraction being substantially free from diethyl succinate and comprising a mixture of diethyl ethoxysuccinate and gamma-butyrolactone, in which said first top fraction is supplied to the second fractionation column, in which said overhead fraction comprises the top fraction from the second fractionation column, and in which said liquid bottom product comprises the bottom product from the first fractionation column.

4. A process according to claim 3, in which a bottom fraction comprising diethyl ethoxysuccinate is recycled from the bottom of the second fractionation column to said first fractionation column.

5. A process according to claim 1, in which the fractionation zone is operated at a pressure in the range of from about 0.01 bar to about 0.75 bar.

6. A process according to claim 1, in which the feed mixture contains from about 99 mole % to about 75 mole % gamma-butyrolactone and from about 1 mole % to about 25 mole diethyl succinate.

7. A process according to claim 1, in which the stream of step (b) is supplied to the fractionation zone so as to provide in the fractionation zone a molar ratio of diethyl ethoxysuccinate:diethyl succinate of from 4:1 to about 200:1.

8. A process for the production of gamma-butyrolactone which comprises:
  (i) hydrogenating a $C_4$ dicarboxylic acid ester feedstock in a hydrogenation zone in the presence of a heterogeneous ester hydrogenation catalyst, said ester feedstock containing a major molar amount of diethyl maleate and a minor molar amount of diethyl succinate;
  (ii) recovering from the hydrogenation zone a crude reaction product that is substantially free from diethyl maleate and contains ethanol, butane-1,4-diol, gamma-butyrolactone, and a minor molar amount of diethyl succinate;
  (iii) distilling the crude reaction product in one or more stages to yield a gamma-butyrolactone-rich fraction containing, in addition to gamma-butyrolactone, a minor amount of diethyl succinate;
  (iv) providing a stream comprising diethyl ethoxysuccinate;
  (v) supplying diethyl ethoxysuccinate of step (iv) and gamma-butyrolactone rich fraction of step (iii) to a fractionation zone;
  (vi) fractionally distilling the gamma-butyrolactone rich fraction of step (iii) in the fractionation zone in the presence of diethyl ethoxysuccinate;
  (vii) recovering as an overhead fraction from the fractionation zone a product stream that is substantially free from diethyl succinate and consists essentially of pure gamma-butyrolactone;
  (viii) recovering from the fractionation zone a liquid bottom product comprising diethyl ethoxysuccinate and diethyl succinate in admixture one with another; and
  (ix) recycling material of the liquid bottom product of step (viii) to form at least a part of the $C_4$ dicarboxylic ester feedstock of step (i).

9. A process according to claim 8, which further includes:
  (x) separating diethyl succinate from the liquid bottom product of step (viii);
  (xi) recovering from step (x) a stream comprising diethyl ethoxysuccinate;
  (xii) recycling diethyl succinate from step (x) to form part of the feedstock of step (i); and
  (xiii) recycling said diethyl ethoxysuccinate containing stream of step (xi) to step (iv).

10. A process according to claim 8, in which the fractionation zone comprises a single fractionation column, in which the gamma-butyrolactone rich fraction of step (iii) is fed to an intermediate part of the fractionation column and in which the stream comprising diethyl ethoxysuccinate of step (iv) is fed to a part of the distillation column above said intermediate part.

11. A process according to claim 7, in which the fractionation zone comprises first and second fractionation columns connected in series, in which the gamma-butyrolactone rich fraction is fed to an intermediate part of the first fractionation column, in which the stream comprising diethyl ethoxysuccinate of step (iv) is fed to a part of the first fractionation column above said intermediate part, in which a first top fraction is recovered from the top of the first distillation column, said first top fraction being substantially free from diethyl succinate and comprising a mixture of diethyl ethoxysuccinate and gamma-butyrolactone, in which said first top fraction is supplied to the second fractionation column, in which said overhead fraction comprises the top fraction from the second fractionation column, and in which said liquid bottom product comprises the bottom product from the first fractionation column.

12. A process according to claim 11, in which a bottom fraction comprising diethyl ethoxysuccinate is recycled from the bottom of the second fractionation column to said first fractionation column.

13. A process according to claim 8, in which the fractionation zone is operated at a pressure in the range of from about 0.01 bar to about 0.75 bar.

14. A process according to claim 8, in which the gamma-butyrolactone rich fraction contains from about 99 mole % to about 75 mole % gamma-butyrolactone and from about 1 mole % to about 25 mole % diethyl succinate.

15. A process according to claim 8, in which the comprising diethyl ethoxysuccinate of step (iv) is supplied to the fractionation zone so as to provide in the fractionation zone a molar ratio with respect to the diethyl succinate present in the gamma-butyrolactone rich fraction of from about 4:1 to about 200:1.

16. A process according to claim 8, in which step (iii) includes recovery of an ethanol containing fraction which is used for reaction with maleic anhydride to produce further diethyl maleate for use in the process.

* * * * *

UNITED STATES PATENT AND TRADEMARK OFFICE
CERTIFICATE OF CORRECTION

PATENT NO.  : 4,945,173
DATED       : July 31, 1990
INVENTOR(S) : Michael A. Wood It is certified that error appears in the above-identified patent and that said Letters Patent is hereby corrected as shown below:

Column 13, line 1, "Connected" should be --connected--.

Column 14, line 52, after "the" insert --stream--.

Signed and Sealed this

Fourth Day of February, 1992

Attest:

HARRY F. MANBECK, JR.

*Attesting Officer*　　　　*Commissioner of Patents and Trademarks*